US006174704B1

(12) United States Patent
Chu et al.

(10) Patent No.: US 6,174,704 B1
(45) Date of Patent: Jan. 16, 2001

(54) METHOD FOR RECOVERY OF PROTEINS PREPARED BY RECOMBINANT DNA PROCEDURES

(75) Inventors: Ruiyin Chu, Roscoe; A. Krishna Mallia, Rockford, both of IL (US)

(73) Assignee: Pierce Chemical Company, Rockford, IL (US)

( * ) Notice: Under 35 U.S.C. 154(b), the term of this patent shall be extended for 0 days.

(21) Appl. No.: 09/220,088

(22) Filed: Dec. 23, 1998

(51) Int. Cl.[7] ............................. C12P 21/06; C12P 21/04
(52) U.S. Cl. ........................ 435/69.1; 435/71.1; 530/412
(58) Field of Search .................. 435/69.1, 71.1; 530/412

(56) References Cited

U.S. PATENT DOCUMENTS 5,118,804 * 6/1992 Defaye et al. ........................ 536/120

OTHER PUBLICATIONS

Rodeghiero et al. Platelet Von Willebrand Factor Assay: Results using Two Methods for Platelet Lysis. Thromb. Res. 59: 259–267, 1990.*

Saito et al. Characteristics of n–octyl D–thioGlucopyroanoside, a new Non–ionic Detergent useful for Membrane Biochemistry. 222: 829–832, 1984.*

Rosenberg, I.M. Protein Analysis and Purification: Benchtop Techniques. Birkhauser, Boston. p. 108–109, 1996.*

Burden et al. Biotechnology: Proteins to PCR. Birkhauser, Boston. p. 69–71, 1995.*

Schutte et al. Pilot–and Process–Scale Techniques for Cell Disruption. Biotechnol. Appl. Biochem. 12: 599–620, 1990.*

* cited by examiner

Primary Examiner—Christopher S. F. Low
Assistant Examiner—Holly Schnizer

(57) ABSTRACT

An improved method is disclosed for the lysis of host cells and extraction of proteins of interest therefrom. The method involves, subsequent to expressing the protein in the host cell by a recombinant DNA procedure, using a reagent solution containing an alkylglycoside or an alkylthioglycoside to lyse the cell to release the protein, and to extract the protein of interest from other host cellular components.

3 Claims, 5 Drawing Sheets

T= Total cell lysate including inclusion bodies and soluble proteins;

I= Pellet containing inclusion bodies;

S= Soluble proteins in the supernatant.

M= Protein Molecular Weight Markers

METHOD FOR RECOVERY OF PROTEINS PREPARED BY RECOMBINANT DNA PROCEDURES

FIELD OF THE INVENTION

The present invention relates to an improved method for the recovery of proteins prepared by recombinant DNA procedures. More particularly, the invention relates to an improved method for the separation and recovery of such proteins from the cellular host in which they have been expressed.

BACKGROUND OF THE INVENTION

Recombinant DNA technology makes it possible to produce large amounts of desired proteins in host cells. To recover a recombinantly produced protein expressed in a host cell, it is first necessary to lyse the cell and then extract the protein from the cellular components. The lysis method should not be harmful to the native characteristics of the protein of interest.

Sonication, French press and enzymatic lysis, either alone or in combination with detergents, are currently available techniques used for cell lysis and protein isolation from host cells. These techniques, however, either require special instrumentation that may not always be available or have other limitations, such as being time consuming or generating heat which can denature certain proteins. Also, the methods, in general, do not permit the recovery of soluble recombinant protein in high yields.

In addition, the available methods do not allow for the optimum recovery of the protein of interest from precipitated dense, granular protein forms, known as inclusion bodies, that are distributed throughout the cytoplasm of the cell. In the expression of some proteins, the inclusion bodies contain high levels of the protein of interest and they can be easily separated from other cytoplasmic proteins by centrifugation. However, using current techniques, it is difficult to extract and purify the protein of interest from the inclusion bodies.

SUMMARY OF THE INVENTION

Now, in accordance with the present invention, there is provided an improved method for the preparation and extraction of a protein of interest, prepared by recombinant DNA techniques, from the host cell in which it is expressed. The improvement finds application in the general method of preparing and isolating a protein from its host cell which involves the steps of expressing the protein in the host cell, lysing the cell to release the protein from the cell, and extracting the protein of interest from other host cell components. The improvement provided by the present invention resides in the use of an aqueous reagent solution consisting essentially of an alkylglycoside or alkythioglycoside to lyse the cell and concurrent therewith to extract the protein of interest from other host cellular components.

The improved method described herein is non-mechanical and accomplished under physiological conditions. Accordingly, the method is gentle and non-disruptive to the protein of interest. It is rapid and easy to accomplish since lysing and extraction occur with the use of a single reagent solution. Of particular significance is the fact that, by practicing the present invention, the protein of interest can be recovered in a higher yield with less manipulative steps than with conventional methods. A related advantage accompanying use of the present invention is that inclusion bodies can be recovered from cellular cytoplasm in a purified form.

DESCRIPTION OF THE PRESENT INVENTION

Figure 1:
FIG. 1 and FIG. 2 illustrate sodium dodecylsulfate-polyarylamide gel electrophorsis (SDS-PAGE) analysis and relative fluorescence, respectively, over five rounds of extraction, of green fluorescent protein (GFP) expressed in E. coli using the reagent solution of the present invention compared with a procedure using sonication.

Important in practicing the present invention is the use of an aqueous reagent solution consisting essentially of an alkylglycoside or alkylthioglycoside to both lyse the host cell to release the protein from the cell and to extract the protein of interest from other host cell components i.e., cell debris such as cell wall and membrane. Glycosides particularly useful herein can be structurally represented as follows:

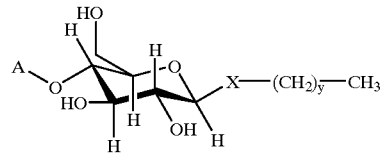

wherein A is the glucose moiety (the glycoside then being a maltoside) or H, X is O or S, and y is an integer between 4 and 12.

The preferred reagent for use herein is octylthioglucoside (A=H, X=S, y=7). This reagent has been described and used for membrane protein solubilization, *Biochem, J.* (1984) 222, 829–832, but not for cell lysis and protein extraction in recombinant DNA procedures.

As used herein in describing the aqueous reagent solution containing the alkylglycoside or alkylthioglycoside, the term "consisting essentially of" means that the glycoside must be present in the solution, but that other constituents which do not adversely effect the use and benefits of the solution can also be present. For example, buffers are generally present in order to maintain a physiological pH of about 7–8. Useful buffers include tris(hydroxymethyl)aminomethane (TRIS), phosphate buffers, 4-(2-hydroxyethyl)-1-piperazineethanesulfonic acid (HEPES), etc.

The desirability of including other constituents in the solution can also be influenced by the protein of interest being expressed. For example, if the protein contains sulfhydryl groups, reducing agents such as dithiothreitol (DDT) or β-mercaptoethanol may be present to keep such groups in reduced form. Protease inhibitors can be included to inactivate enzymes which would adversely effect the sought after protein of interest. Examples of other constituents which may be present are metal chelators to tie up metal impurities and salts of sodium or potassium to maintain molarity.

In further keeping with the present invention, useful amounts of the glycoside included in the aqueous reagent solution are about 0.5% to about 5% (w/v) and preferably about 1 to 2%. About 2 ml to about 20 ml of aqueous reagent solution per gram of wet host cell is useful in accomplishing lysing and extraction. Preferably, about 10 ml of 1% (w/v) aqueous reagent solution per 1 gram of wet host cell is used.

The present invention is useful with respect to the preparation and isolation of any protein capable of being expressed by a recombinant DNA procedure. In practicing the present invention, the reagent solution is added to the wet host cell followed by gentle mixing of a suspension of the wet cells for about 10 minutes at a temperature of about 4° C. to 25° C. Also, the present invention is applicable to proteins produced in a variety of host cells. Bacteria, such as *E.coli*, are particularly convenient host cells for recombinant protein production because bacteria can be grown in very large quantities under well-defined conditions. The invention described herein can also be practiced for the isolation of proteins expressed in yeast, insect and mammalian cells.

The following examples illustrate the present invention. All parts and percentages are by weight unless otherwise specified.

EXAMPLE I

This example illustrates the preparation of bacteria in which 7 different recombinant proteins have been produced. The bacteria are used in subsequent examples illustrating the invention, except for Example III which illustrates the invention in connection with insect cells.

A single colony of *E.coli* transformed with plasmid expressing 6x Histidine-tagged green fluorescent protein (GFP, 28 kDa); glutathione-S-transferase (GST, 25 kDa); dihydrofolate reductase (DHFR, 22 kDa); baculovirus polyhedrin protein (PHD, 30 kDa); rat urate oxidase (UOX, 35 kDa); maltose binding protein (MBP, 45 kDa); and an MBP fusion protein (MBPF, 55 kDa), respectively, was inoculated in 50 ml of Lura-Bertani (LB) medium containing 50 $\mu$g/ml of ampicillin and grown overnight at 30° C. The next morning, the culture was diluted 1:50 into fresh LB medium and incubated at the same temperature for 2–3 hours. The cells were induced by the addition of isopropylthio-$\beta$-D-galactoside (IPTG) to a final concentration of 0.2 mM and the culture was incubated at 30° C. for 12–16 hours. The culture was transferred to 250 ml centrifuge bottles and the bacteria were pelleted by spinning at 7,500×g on a Beckman JA17 rotor. The supernatant was discarded and pellets were used for subsequent experiments.

EXAMPLE II

A reagent solution useful in accomplishing the method of the present invention is prepared by forming an aqueous solution of octylthioglucoside in TRIS buffer, pH 7.5, (1% w/v), hereinafter referred to as the "Reagent Solution". Cells contained in wet *E.coli* pellets prepared in accordance with Example I containing expressed green fluorescent protein (GFP), from 250 ml of culture were suspended in 10 ml of the Reagent Solution and in 10 ml of phosphate buffer saline (PBS). For cell lysis and extraction with the Reagent Solution, the suspension was gently shaken for 10 minutes for a first round of extraction and then two minutes for four subsequent rounds. For lysis with sonication in the PBS buffer, the suspension was sonicated for two minutes with 50% pulse per round. In both cases, after each round of extraction, the soluble proteins were separated from cellular debris by centrifugation at 27000×g for 15 minutes. After the five rounds of extraction, the final pellets (P in FIG. 1) were resuspended in 10 ml of the Reagent Solution or 10 ml of PBS, respectively. For SDS-PAGE analysis, 10 $\mu$l of samples from each extraction were used on 4%–20% gradient gel and stained with GelCode® Blue Stain Reagent (manufactured by Pierce Chemical Company, Rockford, Ill.). The results are exhibited in FIG. 1. In addition, the fluorescence of GFP contained in 100 $\mu$l samples of each extraction described above was measured using a Luminescence Spectrometer (Perkin-Elmer® LS50) and recorded as relative fluorescent units (RFU). The data were processed with Microsoft® Excel and converted to the graph set forth as FIG. 2.

Figure 2:
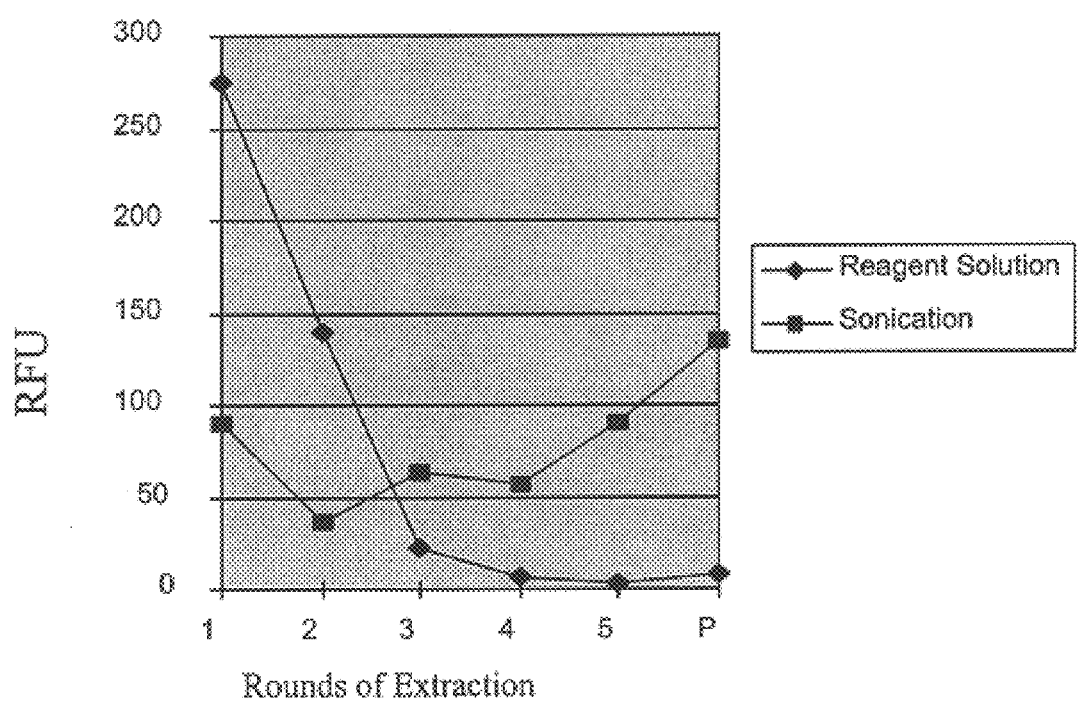

As shown in FIG. 1, using the Reagent Solution of the present invention, at the first round of extraction (Lane 1 in FIG. 1) the majority of the total soluble protein including GFP was recovered, while substantially all of the remaining GFP was recovered in rounds 2, 3, and 4. As illustrated substantially no GFP remained in the pellet(P) after round 5. In contrast, with sonication, substantially the same amount of soluble protein was obtained in each round. FIG. 2 confirms again that, using the method of the present invention utilizing the Reagent Solution, the majority of GFP was recovered in the 1st and 2nd rounds of extraction. In contrast, with the sonication method, even after five rounds of extraction a significant amount of GFP remained in the pellet.

EXAMPLE III

This example illustrates the use of the present invention to lyse and extract protein from insect cells.

Insect Sf9 cells grown in 100 mm plates were infected with a recombinant baculovirus expressing 6×Histidine-tagged GFP. Four days after infection, the culture media were removed and 1 ml of the Reagent Solution described in Example II was added to the plates. Cells from 10 plates were pooled together and the soluble proteins were obtained from the supernatant after centrifugation at 27,000 ×g for 15 minutes on a Beckman JA20 rotor.

EXAMPLE IV

This example illustrates the use of the present invention for the lysis of bacteria containing different recombinantly produced proteins and the purification of these recombinant proteins contained in inclusion bodies.

Figure 3:
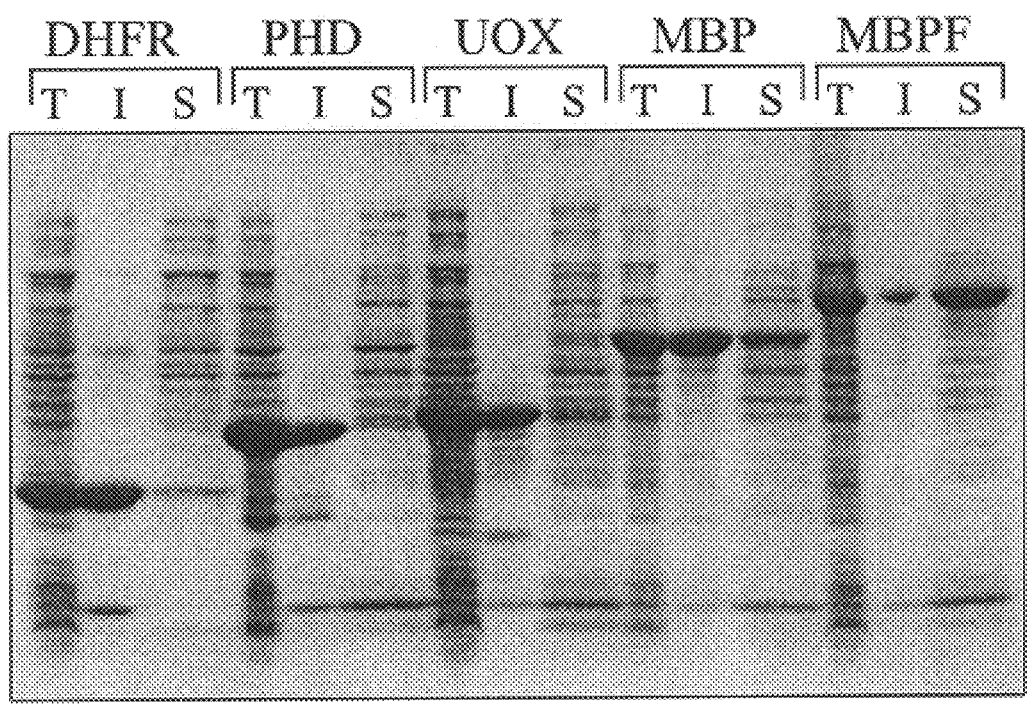
FIG. 3 illustrates SDS-PAGE analysis of the use of the present invention for the extraction of five different recombinant proteins.

Bacterial pellets from a 250 ml of bacterial culture obtained as in Example I were resuspended in 10 ml of the Reagent Solution as prepared in Example II. The soluble and insoluble fractions were separated by centrifugation at 27,000×g for 15 minutes. The supernatant was collected as the soluble protein fraction (S in FIG. 3) and the pellets containing inclusion bodies were resuspended in 10 ml of the Reagent Solution. For removing cell debris (evident in FIG. 1, lane P) from the inclusion body, lysozyme was added to a final concentration of 200 $\mu$g/ml and the suspension was incubated at room temperature for 5 minutes. Then, 100 ml of water was added to the suspension and the inclusion bodies were collected by centrifugation at 27,500×g for 15 minutes. The resulting inclusion bodies (in pellet form) were washed twice with 100 ml of the Reagent Solution, diluted 1:10 in water. The final inclusion body preparations were suspended in 10 ml of H$_2$O and a portion of the preparations were dissolved in 2×SDS-PAGE buffer and subjected to SDS-PAGE analysis. As shown in FIG. 3, the substantial absence of bands in the pellets (lanes I) other than the bands represent the inclusion body illustrate that the inclusion bodies were purified using the process described above employing the Reagent Solution. As can be seen, the purity of inclusion bodies was near 90% for all five different recombinant proteins. As the figure also indicates, the solubility of these five recombinant proteins under the tested conditions are in a order of PHD>UOX>DHFR>MBP>MBPF. Unlike MBPF, which was mostly recovered from the soluble fraction, PHD, UOX, DHFR and MBP were mostly recovered from in insoluble fraction.

EXAMPLE V

This example illustrates the further purification of GST and 6xHistidine-tagged GFP extracted with the Reagent Solution using spin columns.

Figure 4:
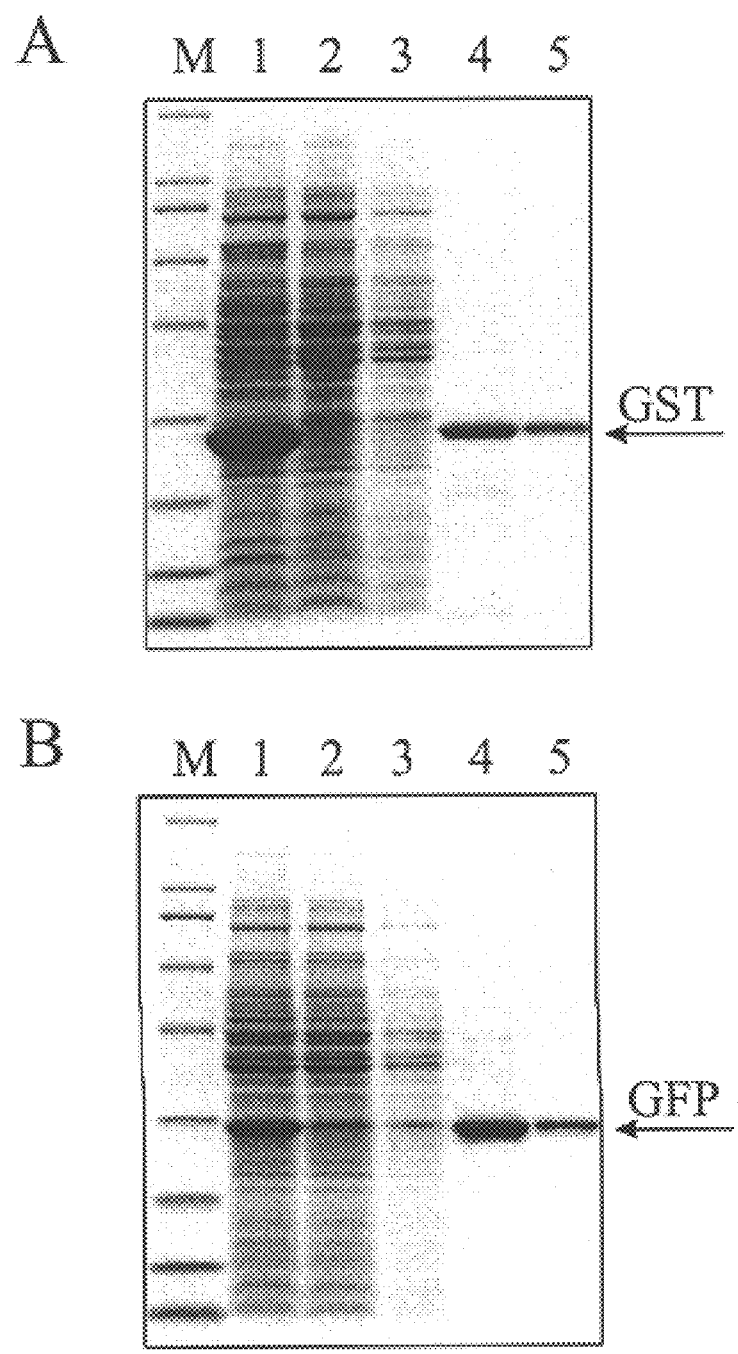
FIG. 4. illustrates SDS-PAGE analysis of the purification of glutathione-S-transferase (GST) and 6x Histidine-tagged green fluorescent protein (GFP) extracted from E. coli using the method of the present invention.

Bacterial pellets expressing GST from 250 ml cultures as prepared in Example I were resuspended in 10 ml the Reagent Solution as prepared in Example II and shaken at room temperature for 10 minutes to ensure complete cell lysis and maximal extraction of soluble proteins. The cellular debris was removed by centrifugation and the supernatant, which contained GST, was incubated with 1.0 ml of Immobilized Glutathione (50% resin) agarose for 10 minutes with gentle shaking. Following centrifugation, the supernatant was discarded and the resin containing bound GST was resuspended in 1 ml of GST Wash Buffer (from Pierce Chemical Company). The resuspended resin was then transferred to 2 spin columns (0.75 ml per spin column) and placed in 2 ml collection tubes. Following a brief spin, the GST protein was eluted with 0.5 ml of 25 mM glutathione (reduced) for four times to achieve complete elution. Similarly, the bacterial lysates as prepared in Example II containing 6xHistidine-tagged GFP was incubated with 1 ml (0.5 ml bed resin) of Nickel charged resin for 10 minutes with gentle shaking. After collecting the affinity gel by a brief, low speed centrifugation, the gel was resuspended in 0.5 ml of 6xHis Wash Buffer and transferred to two spin columns (0.5 ml per column). The columns were washed once with 0.5 ml of 6xHis Wash Buffer to remove contamination and the recombinant 6xHis GFP was eluted four times by 6xHis Elution Buffer. FIG. 4 illustrates the progressive purification of the two proteins. The yield and purity of GST and 6xHis GFP from each elution is shown in Table 1.

TABLE 1

| Proteins | 6xHis GFP Purification | | | | GST Purification | | | |
|---|---|---|---|---|---|---|---|---|
| Elution | 1 | 2 | 3 | 4 | 1 | 2 | 3 | 4 |
| Yield (mg) | 1.6 | 0.8 | 0.25 | 0.1 | 1.5 | 0.7 | 0.3 | 0.1 |
| Purity (%) | 80.7 | 90.0 | 95.1 | 97.8 | 92.0 | 95.1 | 97.0 | 99.1 |

EXAMPLE VI

This example illustrates the further purification of GST extracted in accordance with the present invention using prepacked columns and the comparison with a commercially available purification system based on sonication. The increase in yield is demonstrated by purifying crude lysates using an affinity column and measuring the amount of the bound protein after washing and elution.

One gram of wet bacterial cells expressing GST prepared according to Example I and lysed and extracted according to Example II was further purified using a GST Purification Kit manufactured by Pierce Chemical Company. On another sample of the same bacterial cells, cell lysis and extraction of GST was accomplished using a RediPack™ GST Purifcation Kit manufactured by Amersham Phamacia Biotech Company based on PBS/sonication following the manufacturer's instruction. Both the purification kits use prepacked affinity columns for GST purification from crude lysates. The amount of protein from each purification step was determined by measuring the absorption at $OD_{280}$.

Figure 5:
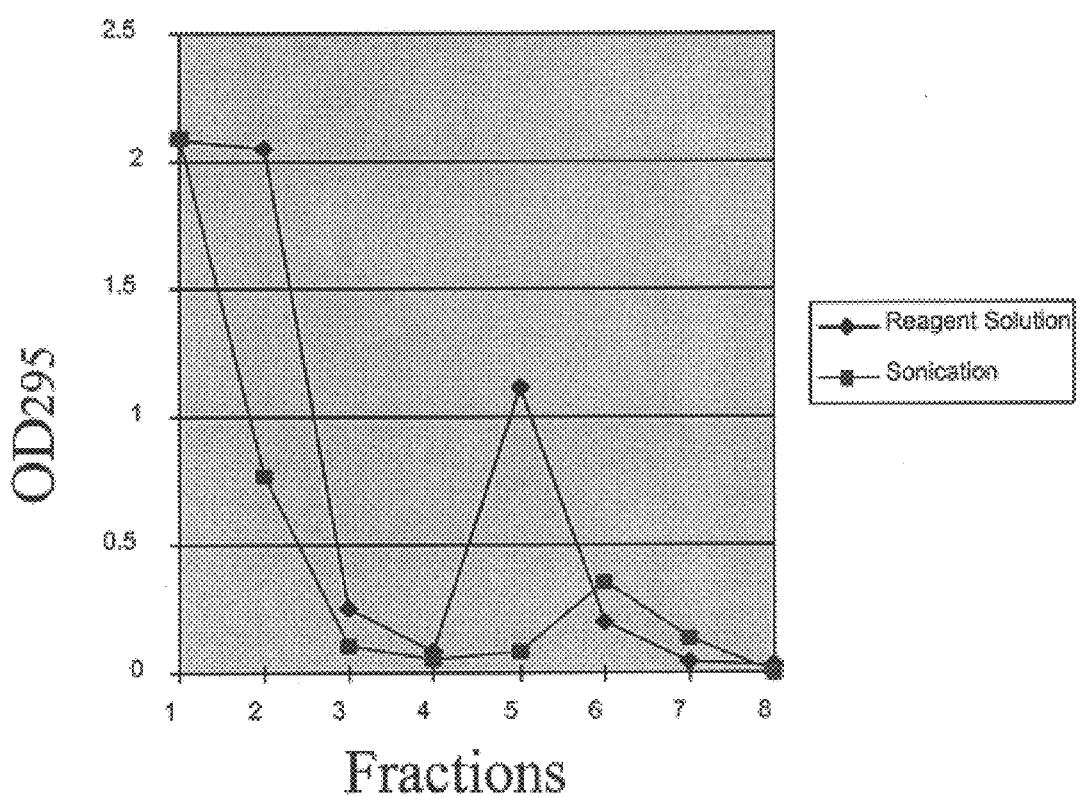
FIG. 5 illustrates the absorbance of 280 nm of proteins in the soluble fractions of the purification steps using the present invention compared with the use of a method as conventionally practiced.

Referring to FIG. 5, the fractions are: 1, total crude lysate; 2, flow through; 3–4, two washes; 5–8, four elutions. As shown, the yield of purified GST (Fractions 5–8) using the improved method of the present invention, is approximately four times higher than that of Amersham Phamacia Biotech Company's product which utilized PBS/sonication for cell lysis and protein extraction. This higher yield is due to higher efficiency of cell lysis and protein extraction when the method of the present invention is used to accomplish the same.

What is claimed is:

1. In a method for the preparation and extraction of a protein of interest prepared by a recombinant DNA procedure from a host bacteria cell comprising expressing the protein in the host cell, lysing the cell to release the protein from the cell, and extracting the protein of interest from other host cellular components; the improvement wherein the cell is lysed and the protein extracted with an aqueous reagent solution consisting essentially of an alkylglycoside or an alkylthioglycoside.

2. The method of claim 1 wherein the glycoside has the following structure:

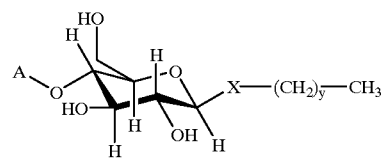

wherein A is the glucose moiety or H, X is O or S, and y is an integer between 4 and 12.

3. The method of claim 2 wherein the glycoside is octylthioglucoside.

* * * * *